United States Patent [19]
Saadat

[11] Patent Number: 5,910,150
[45] Date of Patent: Jun. 8, 1999

[54] APPARATUS FOR PERFORMING SURGERY

[75] Inventor: Vahid Saadat, Redwood Shores, Calif.

[73] Assignee: AngioTrax, Inc., Sunnyvale, Calif.

[21] Appl. No.: 08/863,877

[22] Filed: May 27, 1997

Related U.S. Application Data

[60] Provisional application No. 60/032,196, Dec. 2, 1996.

[51] Int. Cl.⁶ .................................................... A61B 17/32
[52] U.S. Cl. ............................ 606/159; 604/22; 606/170
[58] Field of Search ................................ 606/1, 159, 170, 606/171, 180, 45–49; 604/22

[56] References Cited

U.S. PATENT DOCUMENTS

| Re. 33,258 | 7/1990 | Onik et al. . |
|---|---|---|
| 3,557,794 | 1/1971 | VanPatten . |
| 4,362,161 | 12/1982 | Reimels et al. . |

(List continued on next page.)

FOREIGN PATENT DOCUMENTS

| WO 96/26675 | 9/1996 | WIPO . |
|---|---|---|
| WO 98/05307 | 2/1998 | WIPO . |

OTHER PUBLICATIONS

Cooley, Denton A., M.D. et al., "Transmyocardial Laser Revascularization: Anatomic Evidence of Long–Term Channel Patency," *Texas heart Institute Journal*, vol. 21, No. 3 (1994), pp. 220–224.
Cooley, Denton A., M.D. et al., "Transmyocardial Laser Revascularization: Clinical Experience with Twelve–Month Follow–Up," *The Journal of Thoracic and Cardiovascular Surgery*, (Apr. 1996), pp. 791–799.
Frazier, O.H., M.D., "Myocardial Revascularization With Laser: Preliminary Findings," *Supplement II Circulation*, vol. 92, No. 9, (Nov. 1995), pp. II–58–II–65.
Hardy, Roger Ian, "A Histologic Study of Laser–Induced Transmyocardial Channels," *Laser in Surgery and Medicine*, (1987), pp. 6:563–573.

Hershey, John E. et al., "Transmyocardial Puncture Revascularization: A Possible Emergency Adjunct to Arterial Implant Surgery," *Geriatrics*, (Mar. 1969), pp. 101–108.
Horvath, Keith A., M.D., et al., "Recovery and Viability of an Acute Myocardial Infarct After Transmyocardial Laser Revascularization," *Journal of American College of Cardiology*, vol. 25, No. 1 (Jan. 1995), pp. 258–263.
Horvath, Keith A., M.D., et al., "Transmyocardial Laser Revascularization: Operative Techniques and Clinical Results at Two Years," *The Journal of Thoracic and Cardiovascular Surgery*, (May 1996) pp. 1047–1053.
Kohmoto, Takushi, M.D., "Does Blood Flow Through Holmium: YAG Transmyocardial Laser Channels?," *Ann. Thorac. Surg.*, (1996) pp. 61: 861–868.
Lee, Garrett, M.D., "Effects of Laser Irradiation Delivered by Flexible Fiberoptic System on the Left Ventricular Internal Myocardium," *American Heart Journal*, (Sep. 1983), pp. 587–590.
Sen, P.K. et al., "Further Studies in Multiple Transmyocardial Acupuncture as a Method of Myocardial Revascularization," *Surgery*, vol. 64, No. 5, (Nov. 1968), pp. 861–870.
Thaning, Otto, "Transmyocardial Laser Revascularisation in South Africa," *SAMJ*, vol. 85, No. 8 (Aug. 1995) pp. 787–788.

(List continued on next page.)

*Primary Examiner*—Michael Buiz
*Assistant Examiner*—William W. Lewis
*Attorney, Agent, or Firm*—Fish & Neave; Nicola A. Pisano

[57] ABSTRACT

Apparatus and methods for performing surgery within a hollow-body organ are provided. A catheter is provided having a longitudinal axis and an end region carrying an end effector, the end region movable to a series of positions along the longitudinal axis and with an selectable orientation relative to the longitudinal axis. The catheter includes elements for stabilizing the end region of the apparatus within a hollow-body organ, and for counteracting reaction forces developed during actuation of the end effector. The end effector provides for tissue cutting and aspiration of severed tissue from a treatment site.

34 Claims, 8 Drawing Sheets

U.S. PATENT DOCUMENTS

| | | |
|---|---|---|
| 4,582,056 | 4/1986 | McCorkle, Jr. . |
| 4,640,296 | 2/1987 | Schnepp-Pesch et al. . |
| 4,646,738 | 3/1987 | Trott . |
| 4,729,763 | 3/1988 | Henrie . |
| 4,813,930 | 3/1989 | Elliott . |
| 4,895,166 | 1/1990 | Farr et al. . |
| 4,923,462 | 5/1990 | Stevens . |
| 5,093,877 | 3/1992 | Aita et al. . |
| 5,104,393 | 4/1992 | Isner et al. . |
| 5,106,386 | 4/1992 | Isner et al. . |
| 5,152,744 | 10/1992 | Krause et al. . |
| 5,242,460 | 9/1993 | Klein et al. . |
| 5,281,218 | 1/1994 | Imran . |
| 5,285,795 | 2/1994 | Ryan et al. . |
| 5,323,781 | 6/1994 | Ideker et al. . |
| 5,324,284 | 6/1994 | Imran . |
| 5,330,466 | 7/1994 | Imran . |
| 5,336,237 | 8/1994 | Chin et al. . |
| 5,342,300 | 8/1994 | Stefanadis et al. . |
| 5,354,310 | 10/1994 | Garnic et al. . |
| 5,358,472 | 10/1994 | Vance et al. . |
| 5,358,485 | 10/1994 | Vance et al. . |
| 5,379,772 | 1/1995 | Imran . |
| 5,380,316 | 1/1995 | Aita et al. . |
| 5,383,884 | 1/1995 | Summers . |
| 5,389,073 | 2/1995 | Imran . |
| 5,389,096 | 2/1995 | Aita et al. . |
| 5,403,334 | 4/1995 | Evans et al. . |
| 5,409,000 | 4/1995 | Imran . |
| 5,415,166 | 5/1995 | Imran . |
| 5,439,474 | 8/1995 | Li . |
| 5,443,443 | 8/1995 | Shiber . |
| 5,465,717 | 11/1995 | Imran et al. . |
| 5,488,958 | 2/1996 | Topel et al. . |
| 5,497,784 | 3/1996 | Imran . |
| 5,505,725 | 4/1996 | Samson . |
| 5,507,802 | 4/1996 | Imran . |
| 5,520,634 | 5/1996 | Fox et al. . |
| 5,527,279 | 6/1996 | Imran . |
| 5,554,152 | 9/1996 | Aita et al. . |
| 5,562,694 | 10/1996 | Sauer et al. . |
| 5,569,178 | 10/1996 | Henley . |
| 5,569,284 | 10/1996 | Young et al. . |
| 5,575,772 | 11/1996 | Lennox . |
| 5,575,787 | 11/1996 | Abela et al. . |
| 5,578,067 | 11/1996 | Ekwall et al. . |
| 5,591,159 | 1/1997 | Taheri . |
| 5,601,573 | 2/1997 | Fogelberg et al. . |
| 5,601,586 | 2/1997 | Fucci et al. . |
| 5,601,588 | 2/1997 | Tonomura et al. . |
| 5,607,421 | 3/1997 | Jeevanandam et al. . |
| 5,609,591 | 3/1997 | Daikuzono . |
| 5,609,621 | 3/1997 | Bonner . |
| 5,611,803 | 3/1997 | Heaven et al. . |
| 5,651,781 | 7/1997 | Grace . |
| 5,662,671 | 9/1997 | Barbut et al. .............................. 604/22 |
| 5,724,975 | 3/1998 | Negus et al. . |
| 5,725,521 | 3/1998 | Mueller . |
| 5,830,210 | 11/1998 | Rudko et al. . |

OTHER PUBLICATIONS

Von. Oppell, Ulrich O., "Transmyocardial Laser Revascularisation," *SAMJ*, vol. 85, No. 9, (Sep. 1995), p. 930.

White, Manuel et al., "Multiple Transmyocardial Puncture Revascularization in Refractory Ventricular Fibrillation due to Myocardial Ischemia," *The Annals of Thoracic Surgery*, vol. 6, No. 6, (Dec. 1968), pp. 557–563.

APPARATUS FOR PERFORMING SURGERY

This application claims benefit of Provisional Application 60/032,196 filed Dec. 2, 1996.

FIELD OF THE INVENTION

The present invention relates to apparatus and methods for performing surgery on an interior wall of a hollow-body organ such as the heart, or within the brain cavities and the like. More particularly, the present invention provides a device that enables a clinician to perform surgery on an interior wall of a hollow-body organ at a selected angle relative to a longitudinal axis of the device, and is especially well-suited for boring channels in the myocardium.

BACKGROUND OF THE INVENTION

A leading cause of death in the United States today is coronary artery disease, in which atherosclerotic plaque causes blockages in the coronary arteries, resulting in ischemia of the heart (i.e., inadequate blood flow to the myocardium). The disease manifests itself as chest pain or angina. In 1996, approximately 7 million people suffered from angina in the United States.

Coronary artery bypass grafting (CABG), in which the patient's chest is surgically opened and an obstructed artery replaced with a native artery harvested elsewhere or a synthetic graft, has been the conventional treatment for coronary artery disease for the last thirty years. Such surgery creates significant trauma to the patient, requires long recuperation times, and causes a great deal of morbidity and mortality. In addition, experience has shown that the bypass vessel or graft becomes obstructed with time, requiring further surgery.

More recently, catheter-based therapies such as percutaneous transluminal coronary angioplasty (PTCA) and atherectomy have been developed. In PTCA, a mechanical dilatation device is disposed across an obstruction in the patient's artery and then dilated to compress the plaque lining the artery to restore patency to the vessel. Atherectomy involves using an end effector, such as a mechanical cutting device (or laser) to cut (or ablate) a passage through the blockage. Such methods have drawbacks, however, ranging from re-blockage of dilated vessels with angioplasty to catastrophic rupture or dissection of the vessel during atherectomy. Moreover, these methods may only be used for that fraction of the patient population where the blockages are few and are easily accessible. Neither technique is suitable for the treatment of diffuse atherosclerosis.

A more recent technique which holds promise of treating a larger percentage of the patient population, including those patients suffering from diffuse atherosclerosis, is referred to as transmyocardial revascularization (TMR). In this method, a series of channels are formed in the left ventricular wall of the heart. Typically, between 15 and 30 channels about 1 mm in diameter and up to 3.0 cm deep are formed with a laser in the wall of the left ventricle to perfuse the heart muscle with blood coming directly from the inside of the left ventricle, rather than traveling through the coronary arteries. Apparatus and methods have been proposed to create those channels both percutaneously and intraoperatively (i.e., with the chest opened).

U.S. Pat. No. 5,389,096 to Aita et al. describes a catheter-based laser apparatus for use in percutaneously forming channels extending from the endocardium into the myocardium. The catheter includes a plurality of control lines for directing the tip of the catheter. The patent states that because the myocardium is more easily traversed than the epicardium, the clinician may judge the depth of the channel by sensing the pressure applied to the proximal end of the catheter. The patent does not address the problem of cardiac tamponade that might result if the clinician inadvertently perforates the heart wall, nor how ablated tissue is prevented from embolizing blood vessels. Moreover, Aita et al. rely on fluoroscopic methods to determine the location of the distal end of the catheter. U.S. Pat. No. 5,380,316 to Aita et al. describes an intraoperative laser-based system for performing TMR.

U.S. Pat. No. 5,591,159 to Taheri describes a mechanical apparatus for performing TMR involving a catheter having an end effector formed from a plurality of spring-loaded needles. The catheter first is positioned percutaneously within the left ventricle. A plunger is then released so that the needles are thrust into the endocardium. The needles form small channels that extend into the myocardium as they are withdrawn. The patent suggests that the needles may be withdrawn and advanced repetitively at different locations under fluoroscopic guidance. The patent does not appear to address how tissue is ejected from the needles between the tissue-cutting steps.

The disadvantages of the above-described previously known methods and apparatus for performing TMR are numerous and will impede the acceptance of this new treatment method. For example, percutaneous laser-based systems, such as described in the Aita et al. patent, do not provide the ability to reliably determine the depth of the channels formed by the laser and may result in perforations, nor does that system address potential embolization by the ablated tissue. Laser ablation also causes a significant degree of thermal damage to surrounding tissue, which may be undesirable. In addition, the use of fluoroscopy to determine the exact position of the laser tip within a beating heart is inexact at best. Likewise, previously known mechanical systems such as described in the Taheri patent do not address issues such as rebounding of the needle away from the ventricle wall during deployment or how to remove tissue cores from the needles, and again rely on fluoroscopy to determine the location of the distal tip of device within the heart.

In view of the shortcomings of previously known TMR devices, it would be desirable to provide apparatus and methods for performing percutaneous surgery, such as TMR, that permit precise control of the end region of the device carrying the end effector. Such precise control desirably should, in the context of TMR, include the capability to reliably control the depth of channel formed in the myocardium by the end effector. It would also be desirable to control the location of the end region of the device within the ventricle both with respect to features of the ventricular walls and in relation to other channels formed by the device. In addition, such precise control preferably should include the capability to stabilize the end region of the device within the organ, for example, to counteract reaction forces created by the actuation of the end effector during treatment.

It would also be desirable to provide apparatus for percutaneously performing surgery within a hollow-body organ, such as the heart, that provides for evacuation of tissue removed from the interior of the organ to prevent embolization thereof. It would therefore be desirable to provide an end effector that enables tissue removed from the treatment site to be aspirated.

A number of devices are known in the medical arts that provide certain aspects of the desired functionality. For example, U.S. Pat. Nos. 5,389,073 and 5,330,466 to Imran describe steerable catheters;

U.S. Pat. No. 5,415,166 to Imran describes a device for endocardial mapping; U.S. Pat. No. 4,813,930 to Elliott describes a radially extendable member for stabilizing an angioplasty catheter within a vessel; U.S. Pat. No. 5,354,310 describes an expandable wire mesh and graft for stabilizing an aneurysm; and U.S. Pat. No. 5,358,472 and 5,358,485 to Vance et al. describe atherectomy cutters that provide for aspiration of severed material.

None of the foregoing references, for example, overcomes problems associated with locating an end region of a catheter against a position on the inside wall of a heart chamber. Moreover, the prior art is devoid of a comprehensive solution to the above-noted shortcomings of previously-known apparatus for percutaneously performing surgery, and especially for performing TMR.

SUMMARY OF THE INVENTION

In view of the foregoing, it is an object of this invention to provide apparatus and methods for performing surgery, such as TMR, that permit precise control of an end effector disposed in an end region of the apparatus.

It is another object of this invention to provide apparatus and methods, suitable for use in performing TMR and surgery of other hollow-body organs, that include the capability to reliably control the depth of a channel formed by the end effector, and that provide the location of the end region of the apparatus both with respect to features of the organ and in relation to other channels formed by the apparatus.

It is a further object of this invention to provide apparatus and methods for performing surgery that include the capability to stabilize within the organ an end region of the device carrying an end effector, for example, to counteract reaction forces created by the end effector during treatment.

It is a further object of the present invention to provide apparatus for performing surgery within a hollow-body organ, such as the heart, that permits evacuation of the tissue removed from the interior of the organ to prevent embolization thereof.

It is a further object of the present invention to provide apparatus for performing surgery within a hollow-body organ that reduces the extent of thermal injury to adjacent tissue.

These and other objects of the present invention are accomplished by providing apparatus having a directable end region carrying an end effector for performing surgery. Apparatus constructed in accordance with the present invention comprises a catheter having a longitudinal axis and an end region movable to a series of positions along the longitudinal axis. The end region may be selectively moved to a position at an angle relative to the longitudinal axis of the catheter, including a substantially orthogonal position. The catheter includes means for stabilizing a distal region of the apparatus within a hollow-body organ, and for counteracting reaction forces developed during actuation of an end effector. The catheter also includes means for aspirating tissue cut or ablated from the treatment site by the end effector.

In a preferred embodiment of the apparatus of the invention, the catheter includes a catheter shaft and a guide member disposed for longitudinal sliding movement within a groove of the catheter shaft. The guide member includes an end region including an end effector maneuverable between a transit position wherein the end region lies parallel to a longitudinal axis of the catheter to a working position wherein the end region and end effector are oriented at an angle relative to the longitudinal axis, including a substantially orthogonal position. The end effector preferably includes a mechanical cutting element configured to allow severed tissue to be aspirated to the proximal end of the catheter, and may optionally include an RF electrode for cauterizing the treatment site.

The catheter shaft, which may additionally include adjustable outwardly projecting stabilization members, provides a stable platform to counteract reaction forces generated when the end effector contacts the wall of the hollow-body organ. Methods of using the apparatus of the present invention to perform surgery, such as transmyocardial revascularization, are also provided.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

The present invention relates generally to apparatus and methods for percutaneously performing surgery within a hollow-body organ. The apparatus of the present invention comprises a catheter including a stabilizing catheter shaft which may be disposed within the organ, for example, percutaneously. A guide member engaged with the catheter shaft includes an end region that may be selectively articulated to a position at an angle to a longitudinal axis of the catheter, including a position substantially orthogonal to the longitudinal axis. The end region carries an end effector (e.g., an ablative or mechanical cutting device) for treating tissue. The guide member also permits tissue severed or ablated by the end effector to be aspirated through the catheter to its proximal end for disposal. The catheter shaft, either alone or in conjunction with stabilizing members, and the guide member, provides precise control over the location of the end region, and thus, the end effector.

The present invention therefore offers a device having a directable end region and end effector for performing surgery that provides a degree of control heretofore unattainable. While the invention is described hereinafter as particularly useful in the emerging field of transmyocardial revascularization, apparatus constructed in accordance with the present invention may be advantageously used in performing surgery on other hollow-body organs, such as the intestines, blood vessels or the brain cavities. In addition, while the present invention is described herein in the context of a mechanical cutting system, the control and stabilization apparatus of the present invention may be advantageously used with other types of cutting elements, such as lasers, cryogenic cutters or radio-frequency ablation devices.

Figure 1:
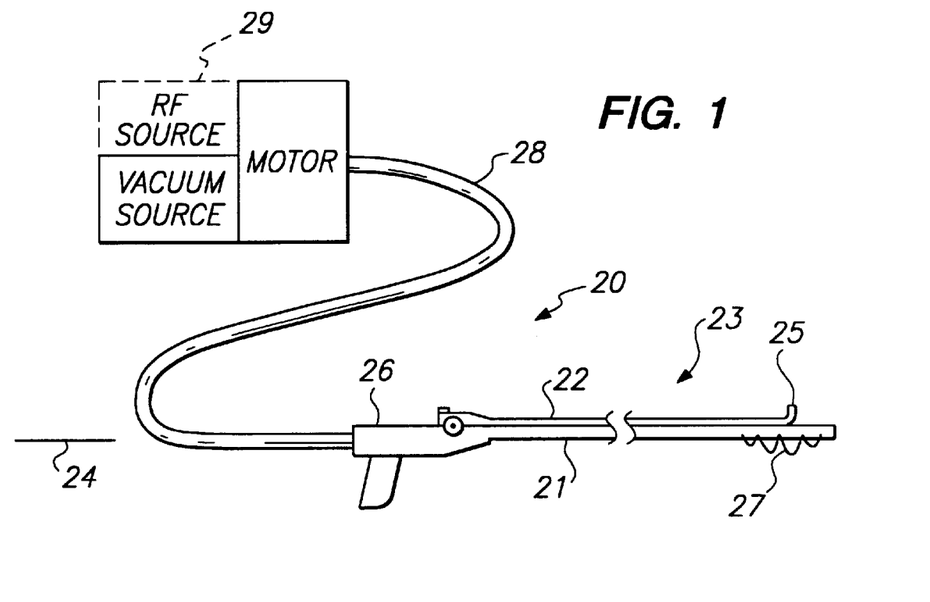
FIG. 1 is a view of a first illustrative embodiment of apparatus constructed in accordance with the present invention.

Referring to FIG. 1, illustrative apparatus 20 constructed in accordance with the present invention is described. Apparatus 20 includes a two-part catheter formed of catheter shaft 21 and guide member 22. Apparatus 20 includes distal region 23 within which guide member 22 has end region 25 that is selectively movable between a transit position parallel to longitudinal axis 24 of catheter shaft 21 and a working position (as shown) substantially orthogonal to longitudinal axis 24. Distal region 23 preferably includes an end effector, described in greater detail hereinbelow, for ablatively or mechanically cutting tissue to attain a treatment goal.

End region 25 of guide member 22 may be positioned longitudinally with respect to catheter shaft 21 by imparting relative movement between guide member 22 and catheter shaft 21 using handle assembly 26. Catheter shaft 21 may include a plurality of stabilizing members 27 to support and stabilize distal region 23 of the apparatus within the hollow-body organ.

Apparatus 20 is coupled via cable 28 to controller 29. In a preferred embodiment wherein the end effector comprises a rotating cutting head, controller 29 includes a motor and control logic for rotating the cutting head responsive to commands input at handle assembly 26 or a footpedal (not shown) and a vacuum source for aspirating severed tissue from the treatment site. Controller 29 optionally may further include RF circuitry (shown in dotted line) for energizing the cutting head to cauterize tissue as it is cut. Alternatively, controller 29 may include a laser source or radio frequency circuitry for causing laser or RF ablation, respectively, using a suitable end effector.

Figure 2:
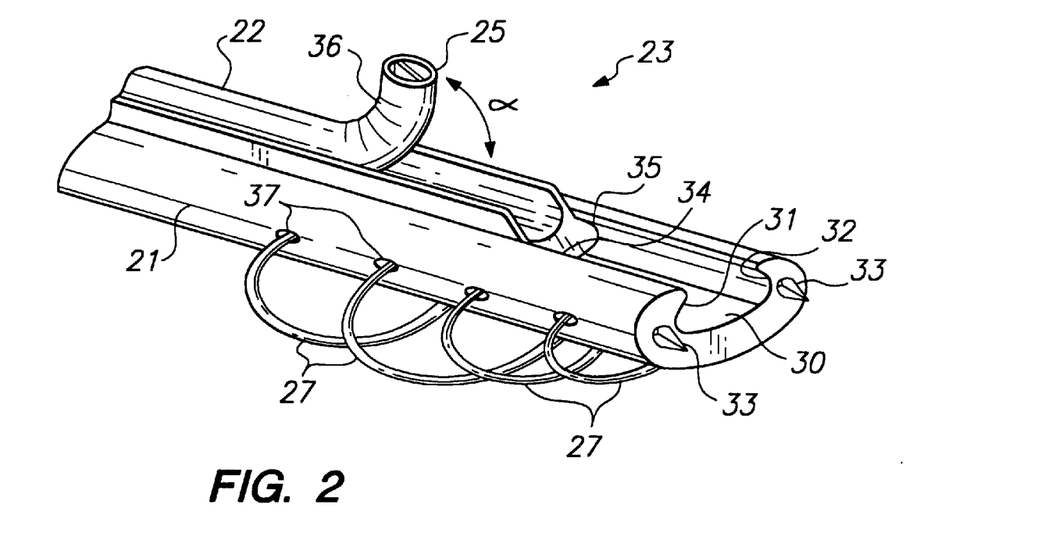
FIG. 2 is a perspective view of the distal region and end effector of the apparatus of FIG. 1.
Figure 3A:
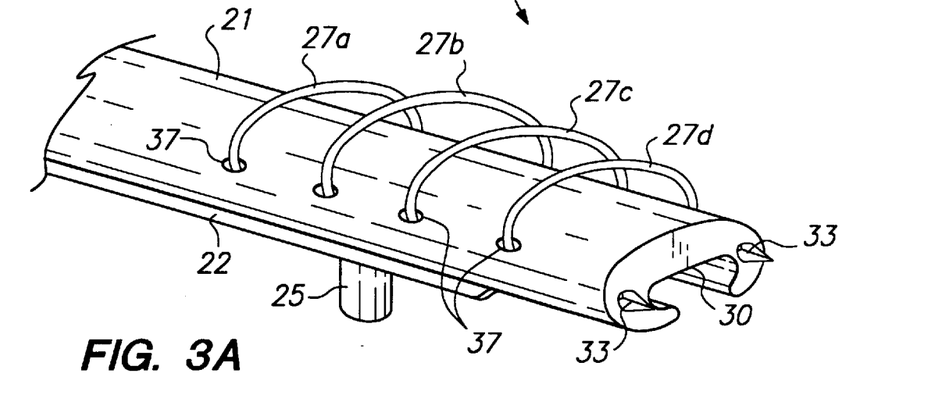
FIGS. 3A and 3B are, respectively, a perspective view and side view of stabilization members disposed on the distal region of the apparatus of FIG. 1.
Figure 3B:
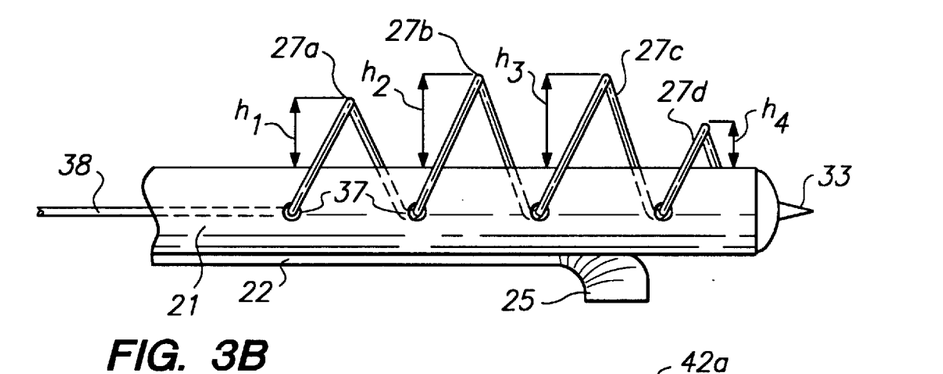

Referring now to FIGS. 2 and 3, distal region 23 of apparatus 20 is described in greater detail. In FIG. 2, distal region 23 includes end region 25 of guide member 22 disposed in sliding engagement in groove 30 of catheter shaft 21. Catheter shaft 21 may be constructed of a flexible material commonly used in catheter products, such as nylon, polyethylene or polyurethane, and contains lateral grooves 31 and 32 that accept a mating portion of guide member 22 in sliding engagement. Catheter shaft 21 may have an ellipsoidal shape to stabilize the catheter shaft and may include two spaced-apart wire stiffeners that terminate in barbs 33. Barbs 33 are designed to engage an interior surface of an organ, for example, the apex of the left ventricle, to reduce rotation of the catheter shaft when the end effector is actuated. Alternatively, catheter shaft 21 may be formed of a material having sufficient stiffness that the wire stiffeners may be omitted over most of the length of the catheter shaft.

Guide member 22 includes end region 25 carrying an end effector and flanges 34 and 35 that slidingly engage grooves 31 and 32. End region 25 may be articulated in region 36 using control wires or a temperature actuated shape-memory alloy steering mechanism, such as described in the aforementioned patents to Imran. Guide member 22 may be constructed of a spring material (commonly called a Bowden) with spaces in-between the coils to allow it to bend when it is pulled by a control wire asymmetrically, as previously known in the art. Alternatively, guide member 22 may be constructed of a stiffer material such as polyimide coated over a braided steel tubular structure, such as employed in previously known neuro-navigational endoscope devices. In this case, slits are provided on the inside of the bend in region 36 so that the guide member bends in the direction of the slits. The slits allow a tight bend radius which may not otherwise be achievable.

Guide member 22 includes a lumen, as described hereinafter, through which tissue may be evacuated from a treatment site by suction. Accordingly, guide member 22 may also be formed from a loosely wound spring reinforced with a soft elastomeric coating. The elastomeric coating advantageously serves the following functions: it provides sealing along the length of the guide member required to maintain adequate suction through the lumen; it prevents collapse of the lumen in the presence of applied suction; it resists kinking of the coils of the spring; and it also enables the guide member to be bent to relatively tight radii. Reinforced tubing suitable for use as guide member 22 is available from Adam Spence Corporation, Wall, N.J.

In the above-described embodiments, end region 25 of guide member 22 is movable from a transit position lying parallel to the longitudinal axis of catheter shaft 21 to a working position wherein end region 25 is articulated to a position substantially orthogonal to the longitudinal axis of the catheter shaft. In addition, end region 25 may be constructed to enable it to be locked in position at any angle $\alpha$ that may be desired for a given application.

With respect to FIGS. 3A and 3B, stabilization members 27 project outwardly from apertures 37 on either side of catheter shaft 21 in distal region 23. Illustratively, stabilization members 27 comprise four circumferentially-oriented hoops formed of flexible wires 27a–27d. In one preferred embodiment, depicted in FIGS. 3, wires 27a–27d comprise a continuous coil having its distal end affixed to catheter shaft 21 and its proximal end connected to handle assembly 26 via push wire 38. The turns of the coil are slidably disposed in lumens within catheter shaft 21 that interconnect apertures 37 on either side of the catheter shaft. When push wire 38 is urged in the distal direction, wires 27a–27d expands outwards by illustrative distances $h_1$–$h_4$ to contact and conform to the topology of the interior wall of the hollow-body organ or vessel. Wires 27a–27d also may be retracted against catheter shaft 21 by pulling push wire 38 in the proximal direction.

Accordingly, wires 27a–27d may be moved from a retracted position in which they are retracted against distal region 23 of catheter shaft 21 to an expanded position in which they engage a wall of the organ and urge end region 25 into engagement with an opposing wall of the organ, thereby stabilizing catheter shaft 21 against rotation.

Stabilization members 27 may be constructed of any suitable elastic material, including stainless steel, spring steel, nickel-titanium alloys, and a variety of plastics. A nickel-titanium alloy is preferred where wires 27a–27d comprise a continuous coil, as in FIG. 3B. In the contracted mode, catheter shaft 21 and guide member 22 have a relatively small profile, for example, 2–3 mm. Upon actuation of the control means in handle assembly 26, wires 27a–27d expand out as shown in FIG. 3B to form a basket shape that spans and conforms to the lumen of the organ or vessel. Where stabilization members 27 comprise a single coil, as in FIG. 3B, they may be actuated by a single control means. Alternatively, as described hereinafter with respect to FIG. 8, each of stabilization members 27 may be individually adjusted to conform to the shape of the cavity of the hollow-body organ. Stabilization members 27 may alternatively be oriented parallel to the longitudinal axis of apparatus 20, as described hereinafter with respect to FIG. 8.

The longitudinal position of end region 25 with respect to catheter shaft 21 may be adjusted by sliding guide member 22 in groove 30 of the catheter shaft. Handle assembly 26 preferably includes means, described hereinafter, for moving guide member with respect to catheter shaft 21 so that end region 25 may be positioned at a series of vertical locations. In addition, stabilization members 27 may be adjusted to provide some control over the lateral positioning of the catheter shaft and guide member with respect to the interior wall of the organ or vessel. Thus, apparatus 20 enables a matrix of treatment sites to be accessed without removing and repositioning the apparatus.

Figure 4:
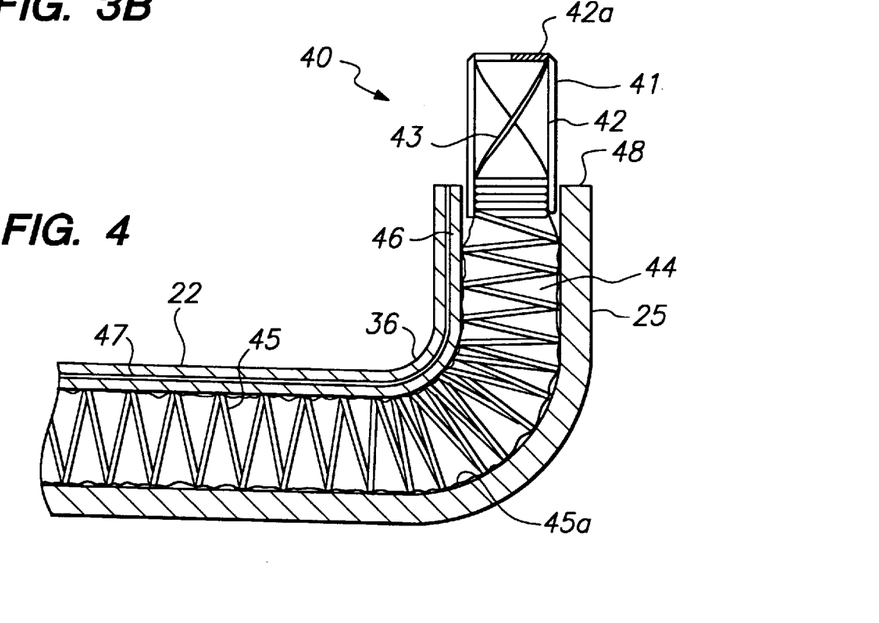
FIG. 4 is sectional view of an illustrative end effector constructed in accordance with the present invention.

Referring now to FIG. 4, end effector 40 (also referred to hereinafter as a "micromorcellator") is described as illustratively comprising a rotary cutting member and drive arrangement. Micromorcellator 40 includes cutting head 41 comprising tubular element 42 within which blade 43 is disposed. Distal edge 42a of tubular element 42 includes a sharpened bevel. Blade 43 is located immediately below, or flush with, distal edge 42a of tubular element 42, and is formed of, for example, a tough plastic, nylon, metal or alloy, such as stainless steel. Blade 43 preferably consists of one turn of a double helix and is designed to cut tissue that protrudes into tubular element 42.

Cutting head 41 is affixed to drive rod 45 so that the helix of blade 43 is rotated in a direction suitable for pushing severed tissue into lumen 44 of drive rod 45. Drive rod 45 preferably includes soft plastic or elastomeric coating 45a, as described hereinabove, to maintain suction through lumen 44. The vacuum source in controller 29 aspirates the severed tissue through lumen 44.

Orientation of end region 25 of guide member 22 is accomplished by control wire 46, which is slidingly disposed in lumen 47 of guide member 22. As described hereinabove, guide member 22 preferably comprises a spring material with spaces in-between the coils to allow it to bend when control wire 46 is retracted in a proximal direction. Alternatively, guide member 22 may be constructed of polyimide coated over a braided steel tube and includes slits on the inside of bend region 36 so that end region 25 bends in the direction of the slits when control wire 46 is retracted in a proximal direction.

Cutting head 41 is connected to the motor of controller 29 via drive rod 45. Drive rod 45 may be formed of a flexible tube such as a bowden or a covered coil or may be formed of a plastic having both high torquability and flexibility. Drive rod 45 is disposed in lumen 44 for a limited range of reciprocation, e.g., up to 3.0 cm, to permit extension of cutting head 41 beyond the end of guide member 22. When end region 25 is in its transit position, cutting head 41 is disposed just below distal endface 48 of guide member 22. Drive rod 45 is hollow and preferably includes a covering of a soft plastic or elastomeric material to allow the application of a negative pressure to aspirate the severed tissue.

Alternatively, helical blade 43 may be extended to the proximal end of guide member 22. In this case, the helical structure will function as an Archimedes screw, so that rotation of the helix pushes severed tissue along the length of the lumen to the proximal end.

Applicant expects that high speed rotation of cutting head 41 will generate frictional heating of the tissue surrounding the cutting head, thereby causing coagulation of the tissue with minimal thermal damage to the surrounding tissue. Alternatively, tubular member 42 of cutting head 41 may comprise an electrically conductive material and be electrically coupled to the optional radio-frequency generator circuitry in controller 29 to provide coagulation of the edges of a channel formed in the tissue by cutting head 41. In this embodiment, tubular element 42 serves as the electrode in a monopolar coagulation arrangement. In addition, a second electrode (not shown) may be formed on the working end spaced apart from the cutting head 41, so that tubular member 42 serves as one electrode of a bipolar coagulation arrangement. Applicant expects that the sealing action produced by RF coagulation, if provided, will simulate the lesions produced by a laser.

Micromorcellator 40 of FIG. 4 may be manufactured, for example, using spring bowden in which the end has been fused with heat to form tubular element 42 and then sharpened to allow it to cut tissue. Blade 43 is inserted into tubular element 42 and bonded to, immediately or a short distance behind, the tip of the sharpened tubular element 42. Tubular member 42 formed thereby may be conductive, or alternatively, a wire may be used to carry RF energy from the RF source to tubular element 42 for providing coagulation, if desired.

Figure 5A:
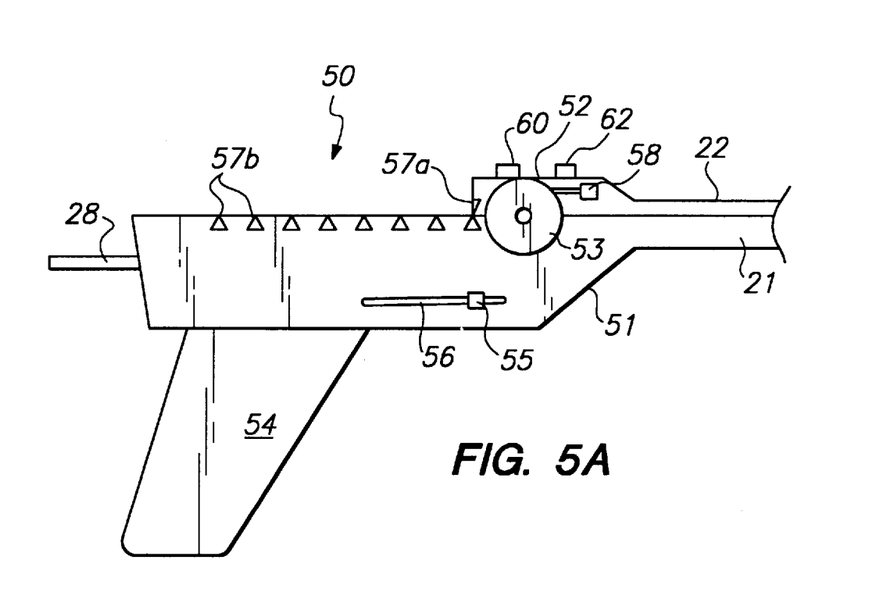
FIGS. 5A and 5B are, respectively, side and perspective views of an illustrative handle assembly for controlling and actuating the apparatus of the present invention.
Figure 5B:
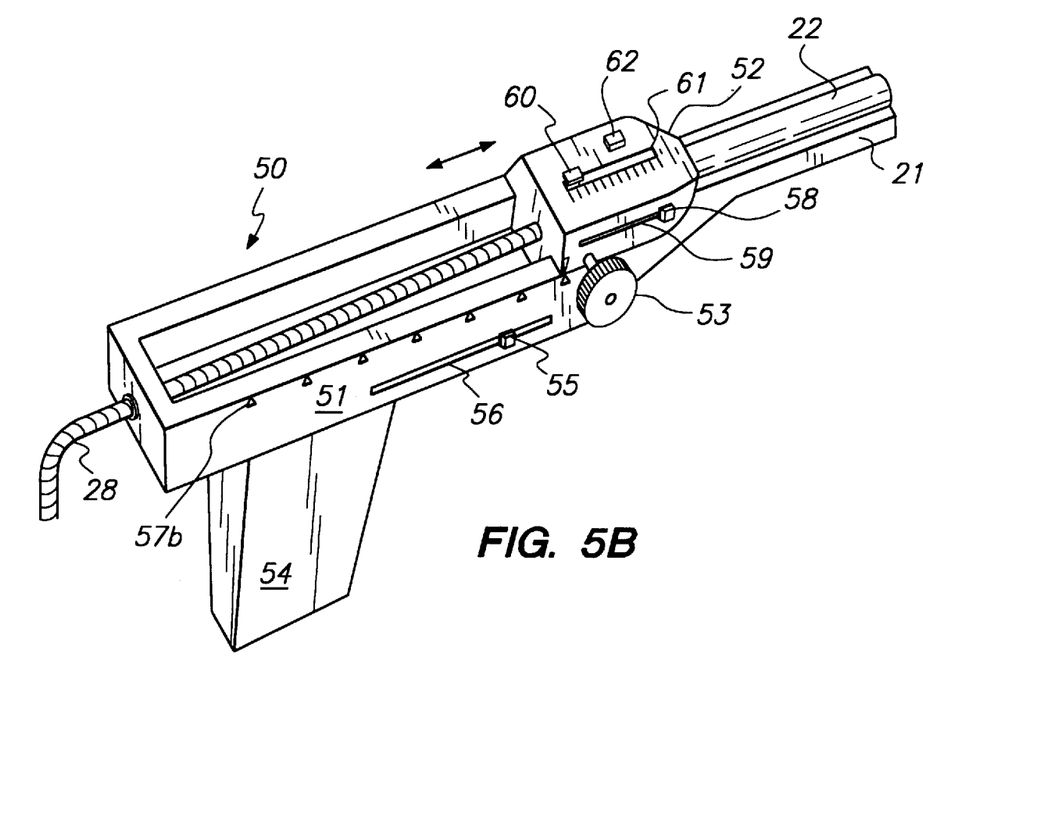

With respect to FIGS. 5A and 5B, illustrative handle assembly 50 is described. Handle assembly 50 includes lower portion 51 affixed to catheter shaft 21 and upper portion 52 affixed to guide member 22. Upper portion 52 is slidingly engaged in lower portion 51, so that guide member 22 may be selectively translated longitudinally with respect to catheter shaft 21 by rotating knob 53. Lower portion 51 of handle assembly 50 includes hand grip 54, and button 55 for controlling the extension of stabilization members 27. Button 55 slides in slot 56 of lower portion 51 to extend or retract stabilization members 27 via push wire 38.

Upper portion 52 includes indicator 57a that may be selectively aligned with indicators 57b, so that the channels formed by end effector 40 are positioned at a series of spaced-apart locations. Cable 28 extends from upper portion 52 and connects the working end of apparatus 20 to controller 29. Upper portion 52 also includes button 58 which may be moved in slot 59 to control the articulation of end region 25 of guide member 22, and depth control lever 60 disposed in slot 61. Depth control lever 60 is moved within slot 61 to control reciprocation of cutting head 41 from end region 25. Slot 61 has a length so that when button 60 is moved to fully extend cutting head 41 from guide member 22, a proximal portion of tubular member 42 remains within guide member 22. In addition, or alternatively, a user-adjustable limit bar (not shown) may be provided in slot 61 to select the maximum extension of cutting head 41 desired for a particular application.

RF button 62 also may be provided to control activation of the optional RF circuitry of controller 29 to coagulate tissue surrounding the channel formed by micromorcellator 40. RF button also could take the form of a microswitch located within slot 61 of handle assembly 50, so as to provide automatic activation of the RF coagulation feature for a short period of time when depth control lever 60 is advanced to contact the user-adjustable limit bar.

It will therefore be seen that handle assembly 50 provides for longitudinal movement of end region 25 with respect to catheter shaft 21 via relative movement between upper portion 52 and lower portion 51 (using knob 53); provides selective deployment of stabilization members 27 via button 55; selective orientation of end region 25 via button 58; control over the depth of the channels formed by end effector 40 via depth control lever 60; and, optionally, activation of an RF coagulation feature via button 62.

Figures 6A, 6B, 6C:
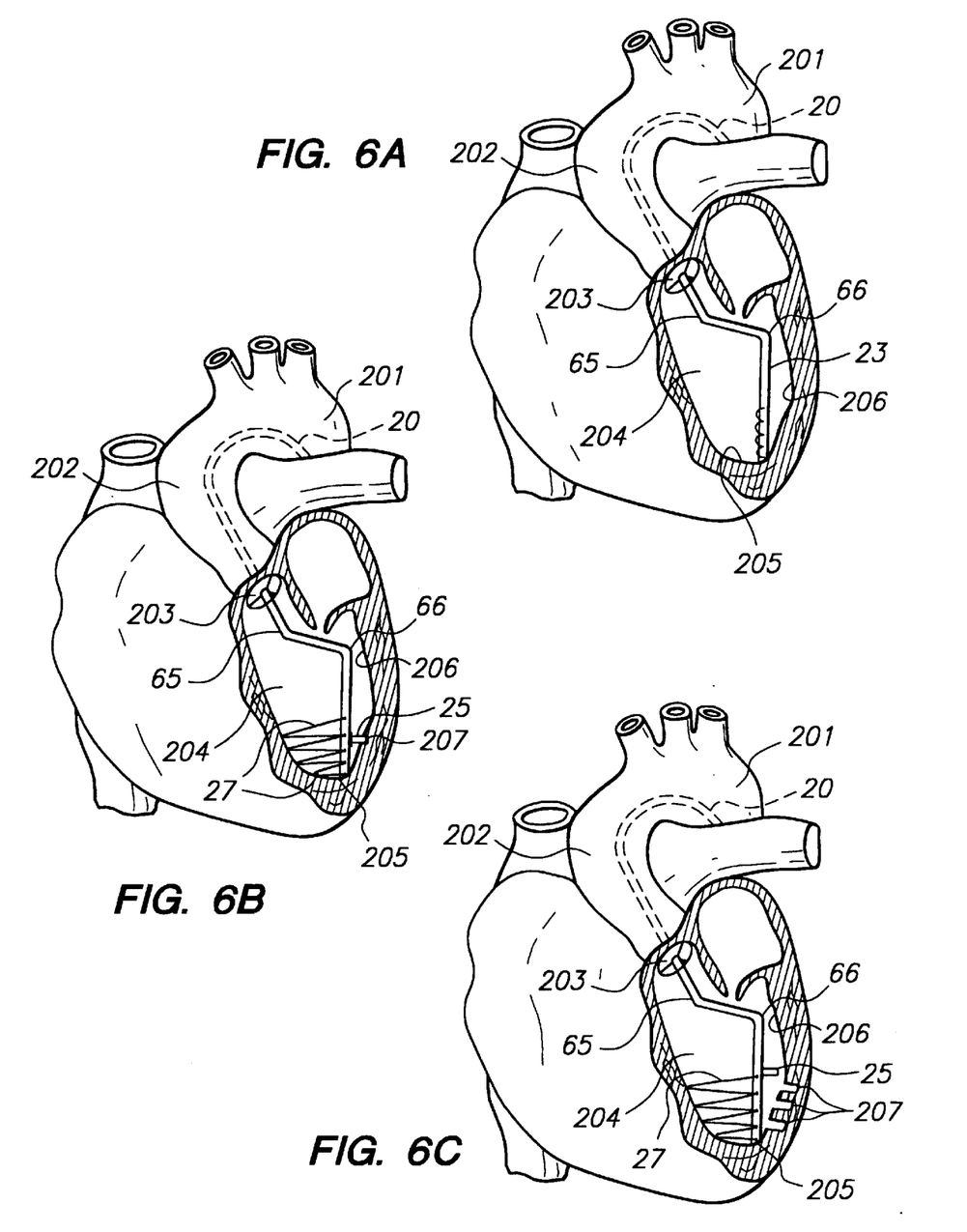
FIGS. 6A–6C are views showing deployment of the apparatus of FIG. 1 in a patient's left ventricle to perform TMR.

Referring now to FIGS. 6A–6C, operation of apparatus 20 in the context of performing transmyocardial revascularization is described. In FIG. 6A, distal region 23 of apparatus 20 is shown positioned in a patient's left ventricular cavity, using techniques which are per se known. Specifically, distal region 23 of apparatus 20 is inserted via a femoral artery, and is maneuvered under fluoroscopic guidance in a retrograde manner up through the descending aorta, through aortic arch 201, and down through ascending aorta 202 and aortic valve 203 into left ventricle 204.

Previously known imaging techniques, such as ultrasound, MRI scan, CT scan, or fluoroscopy, may be used to verify the location of the distal region 23 within the heart. Alternatively, means may be provided in distal region 23 for emitting an ultrasonic signal which is detectable using an ultrasound imaging system outside of the patient. For example, a piezo-electric transducer may be affixed to the tip of the catheter and tuned to a frequency of a color Doppler ultrasound imaging system so as to appear as a bright orange or yellow spot on the display of the ultrasound system. Yet another way to detect the location of distal region 23 is by pinpointing the delay time of an EKG signal at the point of detection, using an electrode disposed in distal region 23. By looking at the morphology as well as the temporal characteristics of the EKG signal, the vertical position of the catheter within the heart chamber may be determined.

Insertion of apparatus 20 into the left ventricle is with guide member 22 in its distal-most position with stabilization members 27 fully retracted and end region 25 in its transit position. As barbs 33 of catheter shaft 21 engage apex 205 of the left ventricle, catheter shaft 21 (and guide member 22) preferentially bends in regions 65 and 66 to form a "dog-leg", in which distal region 23 becomes urged against a lateral wall of the ventricle. Regions 65 and 66 where the bends take place may be made flexurally weaker than the remainder of the catheter shaft to aid in the bending of the catheter at these locations.

Referring to FIG. 6B, button 55 is advanced in slot 56 of handle assembly 50 to extend stabilization members 27 so that they engage the septal wall of the left ventricle and urge the end effector against left ventricular wall 206. The dog-leg bends in regions 65 and 66 allow the catheter to be pushed onto the left ventricular wall while the stabilization members push against the septum. End region 25 of guide member 22 is then rotated to its working position by retracting button 58 along slot 59 of handle assembly 50, thus causing end region 25 to be positioned substantially orthogonally to the longitudinal axis of catheter shaft 21.

The motor and vacuum source of controller 29 are then actuated to cause cutting head 41 to rotate and to induce negative pressure in lumen 44 of micromorcellator 40. The clinician then pushes depth control lever 60 distally in slot 61, causing cutting head 41 to be advanced beyond distal endface 48 of guide member 22 and engage the endocardium. When micromorcellator 40 engages the endocardium, a reaction force is generated in catheter shaft 21 that tends both to push end region 25 away from the tissue and to cause the catheter shaft to want to rotate. The relatively flat configuration of catheter shaft 21, in conjunction with barbs 33, is expected to adequately counteract the torque induced by operation of the micromorcellator. In addition, stabilization members 27 function to counteract both these outward reaction and torque effects.

As micromorcellator 40 is advanced to form channel 207 in the left ventricular wall, tissue severed by cutting head 41 is suctioned into lumen 44 and aspirated to the proximal end of apparatus 20 via the vacuum source of controller 29. The depth of channel 207, which is proportional to the movement of depth control lever 60 in slot 61, may be predetermined using conventional ultrasound techniques, MRI scanning, or other suitable methods. As channel 207 is formed, tissue severed from the ventricular wall is aspirated through lumen 44 of guide member 22, thereby reducing the risk of embolization of the severed material. In addition, applicant expects that the use of suction through lumen 44 will assist in stabilizing the micromorcellator, and tend to draw tissue into the cutting head.

Once micromorcellator 40 has achieved its maximum predetermined depth, cutting head 41 is withdrawn from channel 207 by retracting depth control lever 60 to its proximal-most position, thereby returning cutting head 41 to a position just below distal endface 48 of end region 25 of guide member 22. It is expected that rotation of cutting head 41 will generate sufficient frictional heat in the tissue contacting the exterior of cutting head 41 to coagulate the tissue defining the channel.

Optionally, RF button 62 may be depressed on handle assembly 50 to apply a burst of RF energy to the edges of channel 207 as micromorcellator 40 achieves its maximum predetermined depth, and while cutting head 41 is stationary, rotating or being withdrawn from the channel. If provided, this burst of RF energy is expected to further coagulate the tissue defining the walls of channel 207 and modify the surface properties of the tissue.

As shown in FIG. 6C, a series of vertically aligned spaced-apart channels 207 may be formed in left ventricular wall 207 by sliding upper portion 52 proximally within lower portion 51 of handle assembly 50 (by rotating knob 53). Cutting head 41 is then advanced to form a further channel 207 in the tissue, and the tissue may also be coagulated with a burst of RF energy. When upper portion 52 has been retracted to its proximal-most position, button 55 is adjusted as described above with respect to FIGS. 3A and 3B to cause the catheter shaft to rotate several degrees about its axis. Stabilization members 27 are again extended to contact the septal wall, causing micromorcellator 40 to be urged against left ventricular wall 206 in a region laterally spaced apart from the initial line of channels 207.

The foregoing methods enable a matrix of channels to be formed illustratively in the left ventricular wall. It will of course be understood that the same steps may be performed in mirror image to stabilize the apparatus against the left ventricular wall while actuating the end effector to produce a series of channels in the septal region. In accordance with presently accepted theory, the formation of such channels in the endocardium or septal region enables oxygenated blood in the left ventricle to flow directly into the myocardium and thus nourish and oxygenate the muscle. It is believed that these channels may be drilled anywhere on the walls of the heart chamber, including the septum, apex and left ventricular wall, and the above-described apparatus provides this capability.

Figure 7:
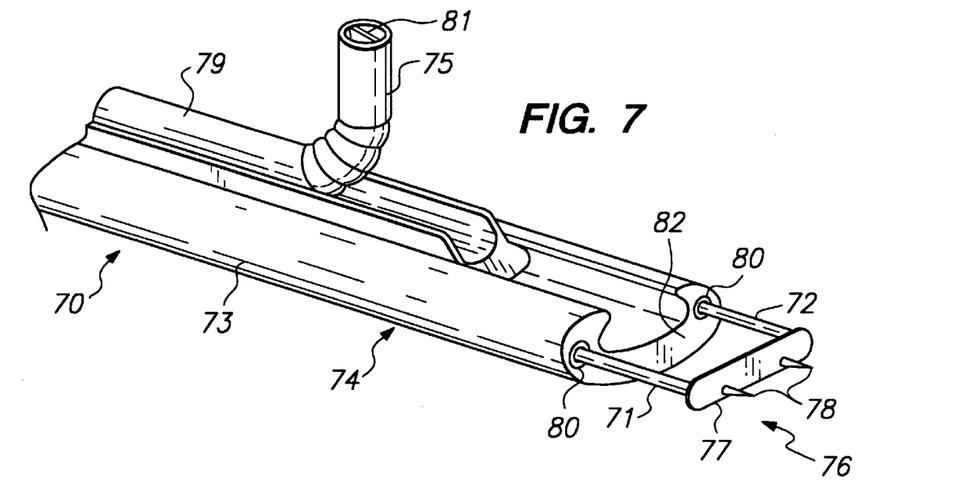
FIG. 7 is a perspective view of the distal region of an alternative embodiment of apparatus constructed in accordance with the present invention.

Referring now to FIG. 7, the distal region of an alternative embodiment of the apparatus of the present invention is described. Apparatus 70 is similar to apparatus 20 described hereinabove, but includes wires 71 and 72 forming a dual-rail on which catheter shaft 73 glides, thereby reducing unwanted rotation of distal region 74 and end region 75. Distal end 76 of the dual-rail includes cushion 77 having barbs 78 for anchoring the catheter shaft in the apex of the left ventricle to prevent inadvertent rotation of catheter shaft 73. Guide member 79 has an inner diameter suitable for carrying one of a variety of end effectors 81, such as a laser fiber, a radio frequency applying device, micromorcellator as described hereinabove, or slit needles, as in the above-mentioned patent to Taheri.

Dual-rail embodiment 70 may be used without stabilization members, or alternatively catheter shaft 73 may include the stabilization members of FIGS. 3 or as described hereinbelow. Wires 71 and 72 also may be formed from a resilient material, e.g., stainless steel or a nickel-titanium alloy, so that when they exit catheter shaft 73 they diverge from one another and give the catheter a larger and more stable base. In this case, cushion 77 preferably comprises an elastomeric material that allows the distance between the tips of wires 71 and 72 to increase beyond the diameter of the catheter. Wires 71 and 72 may have other than circular cross-sections and may take the form of, for example, ribbons.

Wires 71 and 72, in cooperation with a distally-directed axial force exerted on the handle assembly by the clinician, serve to anchor the catheter against a lateral wall of the left ventricle, while catheter shaft 74 and guide member 79 are advanced along the dual-rail. Like apparatus 20, apparatus 70 may include flexurally weaker locations along its length to aid in positioning distal region 74 within the left ventricle.

The dual-rail design of apparatus 70 also may be advantageously employed to determine the location of end region 75 and end effector 81 with respect to the interior of the hollow-body organ or vessel. In this embodiment, wires 71 and 72 are electrically connected within cushion 77 and have a uniform resistance per unit length. Electrodes 80 are positioned in distal end 82 of catheter shaft 73 to measure the resistance of wires 71 and 72 between the electrodes. The resistance between electrodes 80 may be measured, for example, by ohmmeter circuitry, to determine the distance between the distal end 82 of the catheter shaft and the apex of the left ventricle. In conjunction with the displacement between the upper and lower portions of the handle assembly (see FIGS. 5), the position of end region 75 and end effector 81 may be determined relative to the apex of the heart. This position information may be sampled using suitable analog to digital circuitry, and displayed on a display unit to aid the physician in determining where to place the channels in the heart wall.

Figure 8:
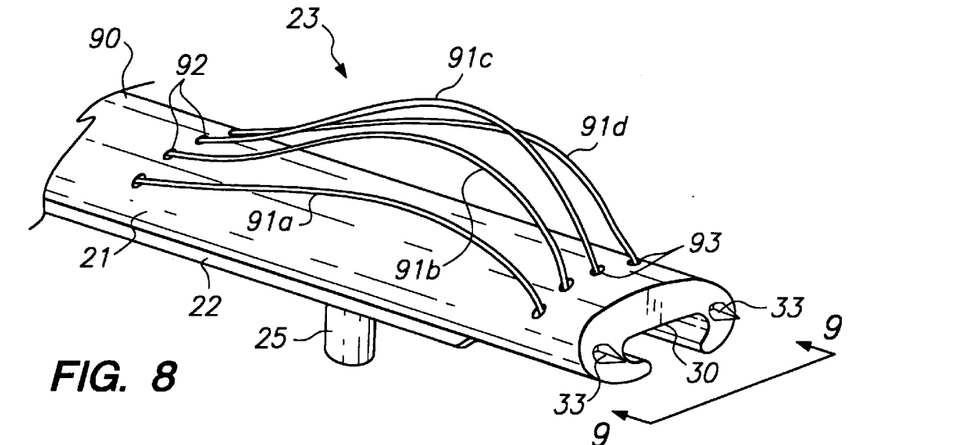
FIG. 8 is a perspective view of the distal region of the apparatus of the present invention showing an alternative embodiment of the stabilization members.

Referring now to FIGS. 8 and 9A–9C, a first alternative embodiment of the stabilization members of the present invention are described. In FIG. 8, the distal region of apparatus 90 similar to that of FIG. 1 is shown, in which like components are indicated by like reference numerals. Apparatus 90 includes catheter shaft 21 including barbs 33 and guide member 22 including end region 25. Stabilization members 91a–91d project from proximal apertures 92 and distal apertures 93, and comprise individual longitudinally-oriented flexible wires. Wires 91a–91d enter lumens in catheter shaft 21 through apertures 92 and extend proximally to handle assembly 26. Each of wires 91a–91d preferably has a respective button (similar to button 55 in FIGS. 5) on handle assembly 26 for selectively controlling the extension of the wires.

Accordingly, wires 91a–91d of the embodiment of FIG. 8 may be moved from a retracted position in which they are retracted against distal region 23 of catheter shaft 21 to an expanded position in which they engage a wall of the organ and urge end region 25 into engagement with an opposing wall of the organ, thus stabilizing catheter shaft 21 against rotation.

Figure 9A:
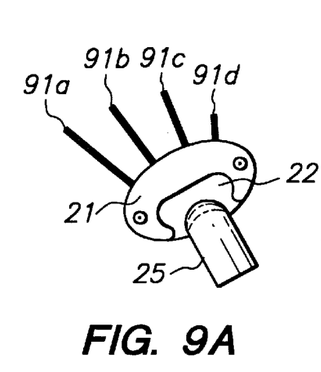
FIGS. 9A, 9B and 9C are end views, taken along view line 9—9 of FIG. 8, depicting various deployment positions of the stabilization members of FIG. 8.
Figure 9B:
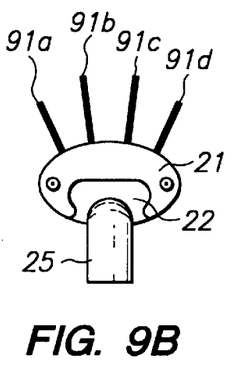
Figure 9C:
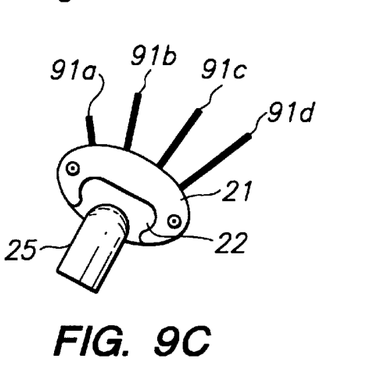

As illustrated in FIGS. 9A–9B, each of stabilization members 91 preferably may be selectively extended a different amount, therefore causing distal region 23 to rotate about its longitudinal axis. For example, in FIG. 9A, wire 91a is extended from distal region 23 a greater distance, causing a larger bow in wire 91a, while wire 91d is extended a smaller distance, causing a smaller bow therein. Consequently, if each of wires 91a–91d contacts a wall of the organ, catheter shaft 23 will have a tendency to rotate in a counterclockwise direction (viewed from the distal end). Conversely, reversing the extensions of wires 91a and 91d, as in FIG. 9C, will cause rotation in the opposite direction. It is therefore seen that by individually controlling the extension of the stabilization members 91, the position of the catheter with respect to an interior lateral wall of the hollow-body organ can be controlled.

Figure 10:
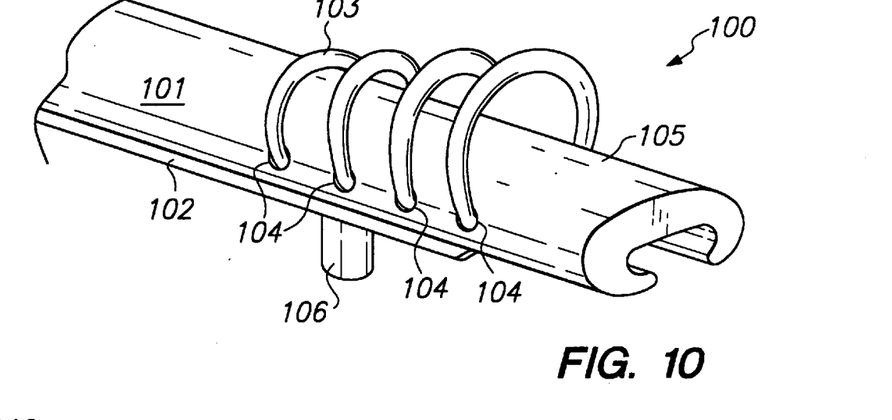
FIG. 10 is a perspective view of the distal region of the apparatus of the present invention showing an alternative embodiment of the stabilization members.
Figure 11:
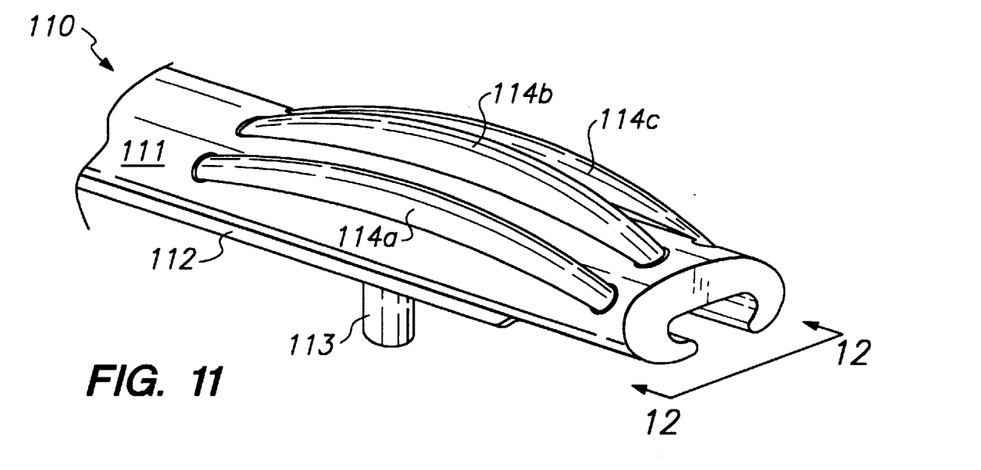
FIG. 11 is a perspective view of the distal region of the apparatus of the present invention showing another alternative embodiment of the stabilization members.

Referring now to FIG. 10 an alternative embodiment of a stabilization arrangement is described. Apparatus 100 includes catheter shaft 101 and guide member 102. Except for stabilization members 103, which in FIG. 10 comprise horizontal inflatable ribs, apparatus 100 is similar to apparatus 20 of FIG. 1.

As described hereinabove, guide member 102 moves relative to catheter shaft 101 to enable the clinician to form a series of vertically aligned channels in the myocardium. Once a line of channels has been formed, the catheter must be moved laterally to a new location and the procedure repeated until the desired number of channels has been achieved. One expedient for doing so, for example, applicable to the apparatus of FIG. 7, is to withdraw the catheter slightly, rotate it and reposition it at a different location on the left ventricular wall. The stabilization arrangement of FIG. 10 instead facilitates lateral movement by deflating ribs 103, rotating catheter shaft 21, and then re-inflating ribs 103.

Specifically, when inflated, stabilization members 103 provide a degree of hoop strength that ensures proper contact of the distal face of end region 106 with the wall of the hollow-body organ or vessel at all times. Once a vertical row of channels has been formed, stabilization members 103 are deflated by the clinician and end region 106 is moved to a new lateral position. The stabilization members are fully re-inflated and another vertical row of channels is formed, as discussed hereinabove.

Figure 12A:
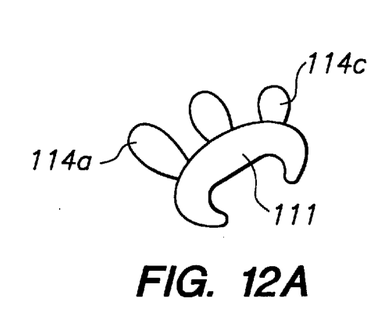
FIGS. 12A–12C are end views, taken along view line 12—12 of FIG. 11, depicting various deployment positions of the stabilization members of FIG. 11.
Figure 12B:
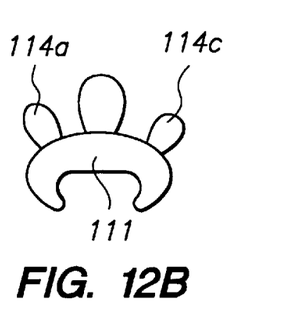
Figure 12C:
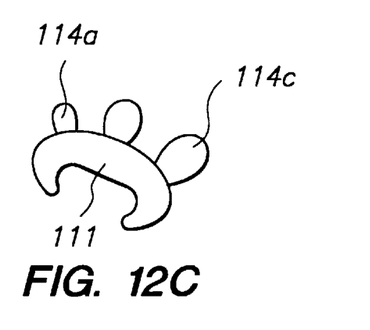

With respect to FIGS. 11 and 12A–12C, another embodiment of the apparatus of the present invention is described in which the stabilization members comprise longitudinally-oriented balloons. Apparatus 110 is otherwise similar to the apparatus of FIG. 8, and includes catheter shaft 111, guide member 112, and end region 113. Stabilization elements 114a14 114c comprise balloons, preferably formed of a compliant material, such as polyurethane, silicone or latex. The handle assembly for apparatus 110 includes valving means for selectively individually inflating balloons 114a–114c. As shown in FIGS. 12A–12C, balloons 114a–114c may be selectively inflated via inflation lumens (not shown) in catheter shaft 111 to stabilize apparatus 110 within a hollow-body organ, and to rotate catheter shaft 111 (and end region 113) in a manner similar to that described above with respect to FIGS. 9A–9C.

Figure 13A:
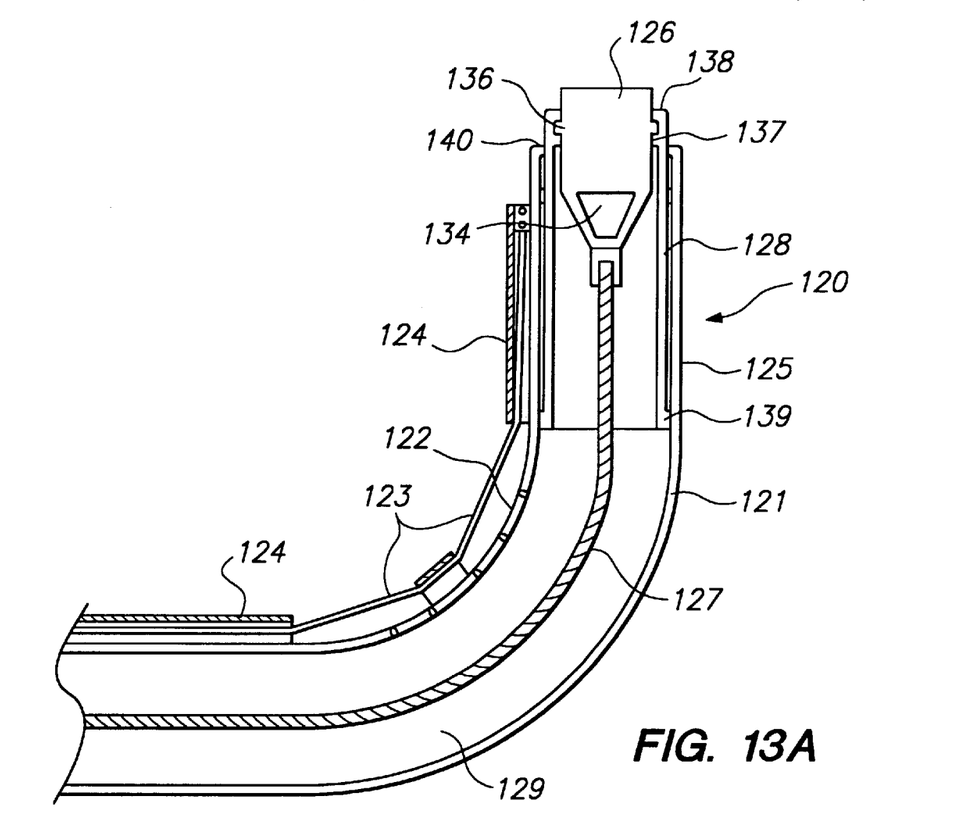
FIGS. 13A and 13B are, respectively, a sectional view of an alternative embodiment of an end effector, and a detailed perspective view of a cutting head arrangement, constructed in accordance with the present invention.
Figure 13B:
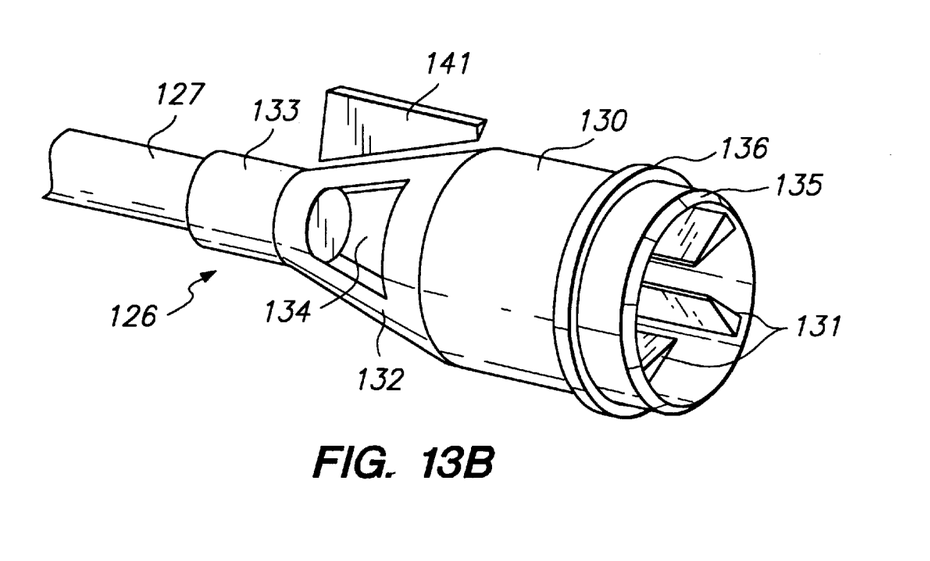

Referring now to FIGS. 13A and 13B, an alternative embodiment of the micromorcellator of the present invention is described. Micromorcellator 120 is disposed within guide member 121 that includes slits in bend region 122 and control wire 123 disposed in lumen 124. End region 125 of guide member 121 is articulated to a position about 90 degrees from the longitudinal axis of the catheter shaft by retracting control wire 123 in a proximal direction, as described hereinabove. Micromorcellator 120 comprises cutting head 126 affixed to a distal end of drive cable 127 and disposed in telescoping tubular member 128. Drive cable 127 is disposed in internal lumen 129 of end region 125, and couples cutting element 126 to the motor of controller 29.

As best seen in FIG. 13B, cutting head 126 includes tubular region 130 and a plurality of angled teeth 131 disposed from its interior wall. Frustoconical portion 132 joins tubular region 130 to drive cable hub 133. Frustoconical portion 132 has openings 134 through which tissue severed by teeth 131 within tubular region 130 exit into lumen 129 of guide member 121. Tubular region includes sharp beveled edge 135 and flange 136 disposed on its exterior surface.

As shown in FIG. 13A, flange 136 is slidingly engaged between steps 137 and 138 of telescoping member 128. Telescoping member 128 also includes flange 139 that abuts against stops 140 when the telescoping member is moved to its distal-most position. Cutting head 126 is reciprocated within lumen 129 of guide member 121 by an axial force applied to drive cable 127 (drive cable 127 is relatively stiff to accomplish this force transmission). When drive cable 127 is pushed in the distal direction (e.g., by the clinician actuating the depth control lever of the handle assembly), cutting head 126 is displaced distally. In addition, because flange 136 is journaled between steps 137 and 138 of telescoping member 128, the telescoping member is advanced (and retracted) along with the cutting head. Accordingly, telescoping member enables cutting head 126 to be extended a distance equal to several times the length of the cutting head while using a centrally disposed drive cable.

Advantageously, cutting head 126 provides the capability to further divide the severed tissue after it is cut from the organ or vessel wall by teeth 131. Teeth 131 preferably are sharp slanted blades mounted on the interior wall of tubular member 130. Teeth 131 are arranged so that they urge the severed tissue in a proximal direction when cutting head 126 is rotated, in conjunction with action of the negative pressure in lumen 129 and forward movement of the cutting head. As the tissue exits tubular region 130 by passing through windows 134, the tissue is further finely divided by the arms of frustoconical region 132 that connect tubular region 130 to drive cable hub 133. Because cutting head 126 is rotated at high speeds, for example 100 to 10,000 rpm, the severed tissue is finely divided by region 132, enhancing the ease with which the tissue may be aspirated through lumen 129.

As illustrated in FIG. 13B, a micromorcellator constructed in accordance with the present invention may optionally include two or more stationary blades 141 (one shown in FIG. 13B), which are preferably fixed to the interior of telescoping member 128 or guide member 121. Tissue exiting windows 134 of cutting head 126 impinge upon stationary blades 141, which further finely divide the tissue. Applicant expects that such further morcellation of the severed tissue will enhance the ability to aspirate the tissue from lumen 129.

Figure 14A:
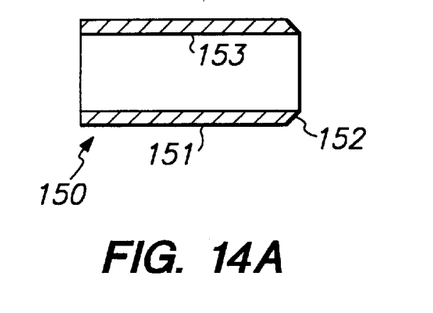
FIGS. 14A–14D are sectional (and for FIG. 14D, perspective sectional) views of further alternative embodiments of cutting heads suitable for use with the present invention.
Figure 14B:
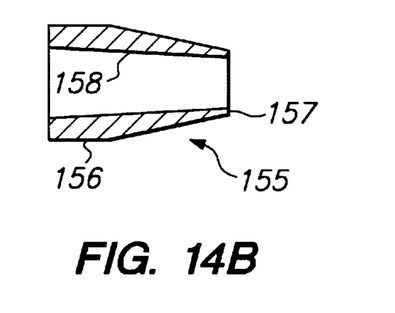

Referring now to FIGS. 14A–14D, further alternative embodiments of cutting heads constructed in accordance with the present invention are described. In FIG. 14A, cutting head 150 comprises tubular member 151 having sharpened beveled edge 152 and lumen 153. Cutting head 150 is similar to cutting head 41 of FIG. 4 (except that blade 43 is omitted) and is attached to the drive rod in a similar fashion. In FIG. 14B, cutting head 155 includes frustoconical tubular member 156 having sharpened edge 157 and lumen 158. Lumen 158 increases in diameter in the distal to proximal directions, so that tissue severed by edge 157 is less likely to become lodged in the lumen. Cutting head 155 is attached to the drive rod in the same manner as, and is operated in a similar manner to, cutting head 41 of FIG. 4.

Figure 14C:
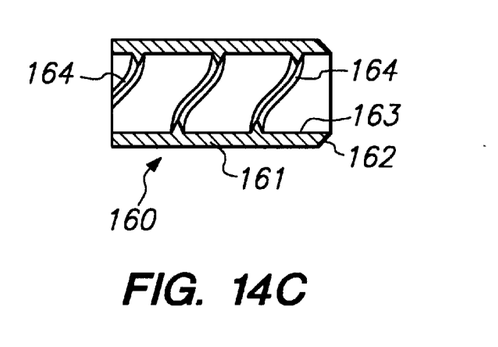

FIG. 14C depicts cutting head 160, which is a variation of cutting head 150, and includes raised thread 164 that projects from the interior wall of lumen 163 of tubular member 161. It is contemplated that the helix of thread 164 should be oriented so that the thread pushes severed tissue in the proximal direction when cutting head is rotated to cut tissue. As will be understood, thread 164 may be equally advantageously employed with cutting head 155 of FIG. 14B.

Figure 14D:
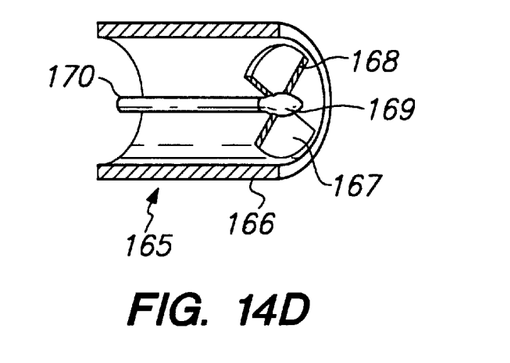

FIG. 14D depicts cutting head 165 comprising tubular member 166, as described with respect to FIG. 14A above, and propeller-like blade 167. Blade 167 includes sharpened edges 168 for severing tissue drawn into tubular member 166, for example, by suction or forward motion of the tubular member. Blade 167 includes nose cone 169, and is mounted on drive cable 170, like the cutting head of FIGS. 13.

Figure 15A:
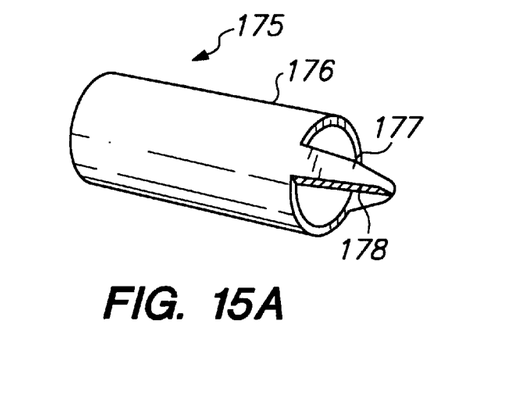
FIGS. 15A and 15B are, respectively, a perspective view and end view of another cutting head suitable for use in the apparatus of the present invention.
Figure 15B:
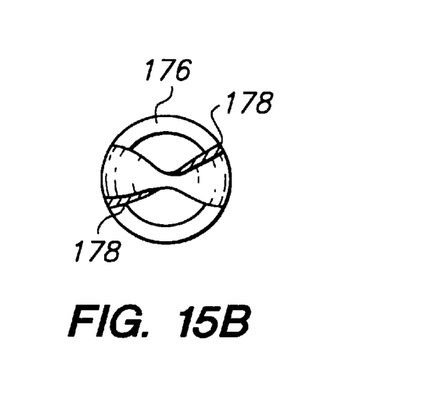

Referring now to FIGS. 15A and 15B, a further alternative embodiment of a cutting head constructed in accordance with the present invention is described. Cutting head 175 comprises tubular member 176 (similar to that of FIG. 14A) carrying band-type blade 177. Blade 177 projects from the distal endface of tubular member 176, and includes a band or ribbon having sharpened lead edges 177. Cutting head 175 is attached to a drive rod in the same manner as, and operated in a similar manner to, cutting head 41 of FIG. 4.

While preferred illustrative embodiments of the invention are described above, it will be apparent to one skilled in the art that various changes and modifications may be made therein without departing from the invention, and the appended claims are intended to cover all such changes and modifications that fall within the true spirit and scope of the invention. For example, one of skill in the art of surgical tools will appreciate that various combinations of the foregoing illustrative cutting heads may be employed in the apparatus of the present invention, and indeed, that end effectors other than those that are mechanically actuated may be advantageously employed with the apparatus and methods of the present invention.

What is claimed is:

1. Apparatus for treating a wall of a hollow-body organ or vessel defining a cavity, the apparatus comprising:
 a catheter shaft adapted for insertion into a cavity, the catheter shaft having a distal region and a longitudinal groove;
 a guide member including an end effector to treat an interior wall of the hollow-body organ, the guide member disposed for translation in the longitudinal groove to define a treatment zone having a length;
 means for disposing the end effector at a selected orientation relative to the catheter shaft within the treatment zone; and
 stabilization means, disposed in the distal region and configured to span the length of the treatment zone, the stabilization means stabilizing the catheter shaft and guide member within the cavity while the end effector treats the wall.

2. The apparatus as defined in claim 1 wherein the stabilization means comprises first and second stiffeners disposed within the catheter shaft.

3. The apparatus as defined in claim 1 wherein the stabilization means comprises at least one barb disposed from a distal endface of the catheter shaft.

4. The apparatus as defined in claim 1 wherein the stabilization means comprises a plurality of stabilizing elements disposed in the distal region, the plurality of stabilizing elements projecting outwardly from the catheter shaft to engage an interior surface of the cavity.

5. The apparatus as defined in claim 4 wherein the plurality of stabilizing elements may be adjusted between a contracted state and an expanded state.

6. The apparatus as defined in claim 4 wherein the plurality of stabilizing members are individually controllable.

7. The apparatus as defined in claim 4 wherein the plurality of stabilizing elements comprises elastic wires or ribbons.

8. The apparatus as defined in claim 7 wherein the elastic wires or ribbons comprise portions of a continuous coil.

9. The apparatus as defined in claim 4 wherein the plurality of stabilizing elements comprises inflatable members.

10. The apparatus as defined in claim 1 wherein actuation of the end effector forms a channel in an interior wall of the cavity.

11. The apparatus as defined in claim 10 further comprising means for aspirating material removed from the interior wall upon actuation of the end effector.

12. The apparatus as defined in claim 10 wherein the end effector includes a rotating cutting head.

13. The apparatus as defined in claim 12 wherein the end effector is electrically conductive, the apparatus further comprising means for delivering radio-frequency energy to the end effector to coagulate tissue defining the channel.

14. The apparatus as defined in claim 1 further comprising means for detecting the position of the end effector relative to a distal end of the catheter shaft.

15. The apparatus as defined in claim 1 further comprising means for detecting the position of the end effector relative to a distal end of the catheter.

16. Apparatus for performing transmyocardial revascularization comprising:
 a catheter configured for insertion into a cardiac chamber, the catheter having a distal endface including a portion configured to engage an apex of the cardiac chamber;
 a guide disposed for translation along the catheter to a plurality of treatment positions, the guide including an end region movable from a transit position aligned with a longitudinal axis of the catheter to a working position at an angle relative to the longitudinal axis;
 an end effector disposed within the end region of the guide to form a channel in an endocardial surface; and
 a stabilizing element disposed on the distal region of the catheter, proximal of the distal endface, the stabilizing element configured to engage an interior surface of a cardiac chamber to stabilize the distal region during operation of the end effector.

17. The apparatus as defined in claim 16 wherein the stabilizing element comprises first and second stiffeners disposed within the catheter shaft.

18. The apparatus as defined in claim 16 wherein the distal endface comprises at least one barb disposed from a distal endface of the catheter shaft.

19. The apparatus as defined in claim 16 wherein the stabilizing element comprises a plurality of members disposed in the distal region, the plurality of members projecting outwardly from the catheter shaft to engage an interior surface of the cavity, the plurality of members adjustable between a contracted state and an expanded state.

20. The apparatus as defined in claim 19 wherein the plurality of members are individually controllable.

21. The apparatus as defined in claim 19 wherein the plurality of members comprise portions of a continuous coil.

22. The apparatus as defined in claim 16 further comprising means for aspirating material removed from the wall of the hollow-body organ by the end effector.

23. The apparatus as defined in claim 16 wherein the end effector is electrically conductive, the apparatus further comprising means for delivering radio-frequency energy to the end effector to coagulate tissue defining the channel.

24. Apparatus for performing transmyocardial revascularization, the apparatus comprising:
 a catheter configured for transluminal insertion into a cardiac chamber, the catheter having a distal region and first and second regions configured to preferentially bend to dispose the distal region towards an endocardial surface,
 an end effector configured to bore a channel in the endocardial surface at a treatment position;
 means for disposing the end effector at a selected orientation relative to the endocardial surface; and
 stabilization means, disposed in the distal region of the catheter, for stabilizing the catheter within the cardiac chamber, the stabilization means stabilizing the catheter and end effector while the end effector bores a channel in the endocardial surface.

25. The apparatus as defined in claim 23 wherein the stabilization means comprises first and second stiffeners disposed within the catheter.

26. The apparatus as defined in claim 24 wherein the stabilization means comprises at least one barb disposed from a distal endface of the catheter.

27. The apparatus as defined in claim 24 wherein the stabilization means comprises a plurality of stabilizing elements disposed in the distal region, the plurality of stabilizing elements projecting outwardly from the catheter to engage an interior surface of the cardiac chamber.

28. The apparatus as defined in claim 27 wherein the plurality of stabilizing elements may be adjusted between a contracted state and an expanded state.

29. The apparatus as defined in claim 27 wherein the plurality of stabilizing members are individually controllable.

30. The apparatus as defined in claim 27 wherein the plurality of stabilizing elements comprises elastic wires or ribbons.

31. The apparatus as defined in claim 30 wherein the elastic wires or ribbons comprise portions of a continuous coil.

32. The apparatus as defined in claim 27 wherein the plurality of stabilizing elements comprises inflatable members.

33. The apparatus as defined in claim 24 further comprising means for aspirating material removed from the channel upon actuation of the end effector.

34. The apparatus as defined in claim 24 wherein the end effector is electrically conductive, the apparatus further comprising means for delivering radio-frequency energy to the end effector to coagulate tissue defining the channel.

* * * * *